(12) United States Patent
Griggio et al.

(10) Patent No.: US 10,929,507 B2
(45) Date of Patent: Feb. 23, 2021

(54) APPARATUS AND METHOD FOR COLLECTING MEDICAL DATA

(71) Applicant: NEXT SIGHT S.R.L., Pordenone (IT)

(72) Inventors: Paola Griggio, Pordenone (IT); Flavio Rizzardi, Pordenone (IT)

(73) Assignee: NEXT SIGHT S.R.L., Pordenone (IT)

( * ) Notice: Subject to any disclaimer, the term of this patent is extended or adjusted under 35 U.S.C. 154(b) by 600 days.

(21) Appl. No.: 14/915,144

(22) PCT Filed: Aug. 25, 2014

(86) PCT No.: PCT/IT2014/000225
§ 371 (c)(1),
(2) Date: Feb. 26, 2016

(87) PCT Pub. No.: WO2015/029082
PCT Pub. Date: Mar. 5, 2015

(65) Prior Publication Data
US 2016/0210409 A1    Jul. 21, 2016

(30) Foreign Application Priority Data

Aug. 26, 2013 (IT) .......................... VI2013A000216

(51) Int. Cl.
*G16H 10/60* (2018.01)
*A61B 3/12* (2006.01)
(Continued)

(52) U.S. Cl.
CPC .......... *G06F 19/321* (2013.01); *A61B 3/0033* (2013.01); *A61B 3/12* (2013.01); *G16H 10/60* (2018.01)

(58) Field of Classification Search
CPC ........ G16H 10/60; A61B 3/12; A61B 3/0033; G06F 19/321
See application file for complete search history.

(56) References Cited

U.S. PATENT DOCUMENTS 7,524,062 B2 *  4/2009  Iwa .......................... A61B 3/12
                                                          351/206
2004/0034550 A1  2/2004  Menschik
(Continued)

OTHER PUBLICATIONS

Notification of Transmittal of the International Search Report and the Written Opinion of the International Searching Authority dated Dec. 16, 2014.
(Continued)

*Primary Examiner* — Robert A Sorey
*Assistant Examiner* — Kristine K Rapillo
(74) *Attorney, Agent, or Firm* — Hedman & Costigan, P.C.; James V. Costigan; Kathleen A. Costigan

(57) ABSTRACT

An apparatus and method for collecting medical data which envisages:
  acquiring medical data by means of a medical data collecting apparatus (10);
  storing a copy of said medical data in a remote device (16), separate from the apparatus (10);
  assessing the methods of use of the apparatus (10) by means of a predefined algorithm comparing the medical data comprised in the last copy stored and the medical data comprised in the penultimate copy stored of the medical data;
  limiting or blocking functioning of the apparatus (10) if the methods of use assessed correspond with predefined prohibited methods of use.

16 Claims, 1 Drawing Sheet

(51) Int. Cl.
   *G06F 19/00*      (2018.01)
   *A61B 3/00*       (2006.01)

(56)          References Cited

U.S. PATENT DOCUMENTS

2007/0083286 A1*  4/2007  Kobayashi ............. G16H 40/20
                                                        700/214
2007/0195267 A1   8/2007  Franz
2008/0306872 A1* 12/2008  Felsher ................ G06Q 20/367
                                                         705/51
2009/0019065 A1   1/2009  Sapounas
2012/0226771 A1*  9/2012  Harrington ......... G06F 19/3418
                                                        709/217

OTHER PUBLICATIONS

Italian Patent Office Search Report and Written Opinion dated May 6, 2014 (partially in English).
Letter from Italian Patent Office dated May 27, 2014.

* cited by examiner

APPARATUS AND METHOD FOR COLLECTING MEDICAL DATA

The present invention relates to an apparatus and method for collecting medical data.

In particular, the present invention relates to a device and a method of acquisition of ophthalmoscopic data and particularly data comprising images of the ocular fundus.

The present invention therefore relates to the field of medical devices and, in particular, the field of optical devices for inspection of the eye.

Nowadays, in the field of acquisition of images of the ocular fundus, devices are known, commonly called fundus camera, which are able to photograph the ocular fundus of a user.

Said devices comprise a device for acquisition of digital images, adapted to photograph the ocular fundus, and an electronic storage device of data in electronic format.

The storage device allows the operator to save in a database each photograph associated with the patient entered beforehand by said operator.

This traditional device has the disadvantage of not allowing organised management of the data.

In fact, when a doctor is unable to use the device which contains the data on his own patients, for example because he/she is in a medical clinic which is not the one where said device is installed or because it is not working, said doctor must save the data of the examination on a support and then enter it into the database of the device, or must take a copy of said database with him, when it is possible to enter the new data directly, with the consequent risk of losing the data or comprising its security.

The problem underpinning the present invention is proposing a device and a method for collecting medical data and particularly ophthalmoscopic data which allows these problems to be overcome.

The main task of the present invention is producing a device and a method for collecting medical data which provides a solution to said problem.

Within the scope of this task an object of the present invention is to propose a device and a method for collecting medical data and particularly ophthalmoscopic data which allows remote access to the ophthalmoscopic data collected.

A further object of the present invention is producing a device and a method for collecting medical data and especially ophthalmoscopic data which allows selective access to the data collected as a function of predefined privileges of the operator accessing it.

Another object of the invention is proposing a device and a method for collecting medical data and particularly ophthalmoscopic data which allows protection of sensitive information on users to which said medical data refers.

This task, as well as these and other objects that will more fully emerge below, are reached through a device and a method for collecting medical data according to the appended independent claims which are incorporated fully herein for reference purposes.

Detailed characteristics of the device and the method for collecting medical data according to the invention are reported in the dependent claims.

In practice, a device and a method for collecting medical data according to the present invention solve the above problem by combining:

calculation of medical data acquisition performed by a specific operator by means of any device according to the present invention, and the fact that the medical data acquired from each device according to the present invention is stored on a remote server, and therefore accessible to the operator by means of any device according to the invention.

It is clear that the medical data will preferably be transmitted to the remote server and/or stored there in encrypted form and advantageously access criteria will be provided which will make available to a user of the remote server only certain predefined types of information contained in said data, selectively as a function of the access credentials.

In other words, by means of a device and a method for collecting medical data according to the present invention, an operator may acquire medical data or access previously acquired medical data, stored on the server, by means of any device according to the present invention, since the costs paid relate exclusively to the effective amount of data acquired, irrespective of the number of different devices according to the invention by means of which said data has been acquired.

In other words, a device and a method for collecting medical data according to the present invention allows a more efficient management of resources for doctors' surgeries and professionals in the medical field.

In fact, the partners of a doctor's surgery may use a single medical data collecting device, allowing data to be acquired, by means of said device, which is only accessible to the doctor who acquired it and not to his colleagues, unless they have prior authorisation. Furthermore, an individual doctor can acquire medical data on his own patients by means of any medical data collecting device according to the invention, thus being unconnected to the structure of his own surgery.

Further characteristics and advantages of the invention will more fully emerge from the description of a preferred but not exclusive embodiment of an apparatus and a method for collecting medical data according to the invention, illustrated by way of non-limiting example in the accompanying drawings, in which.

Figure 1:
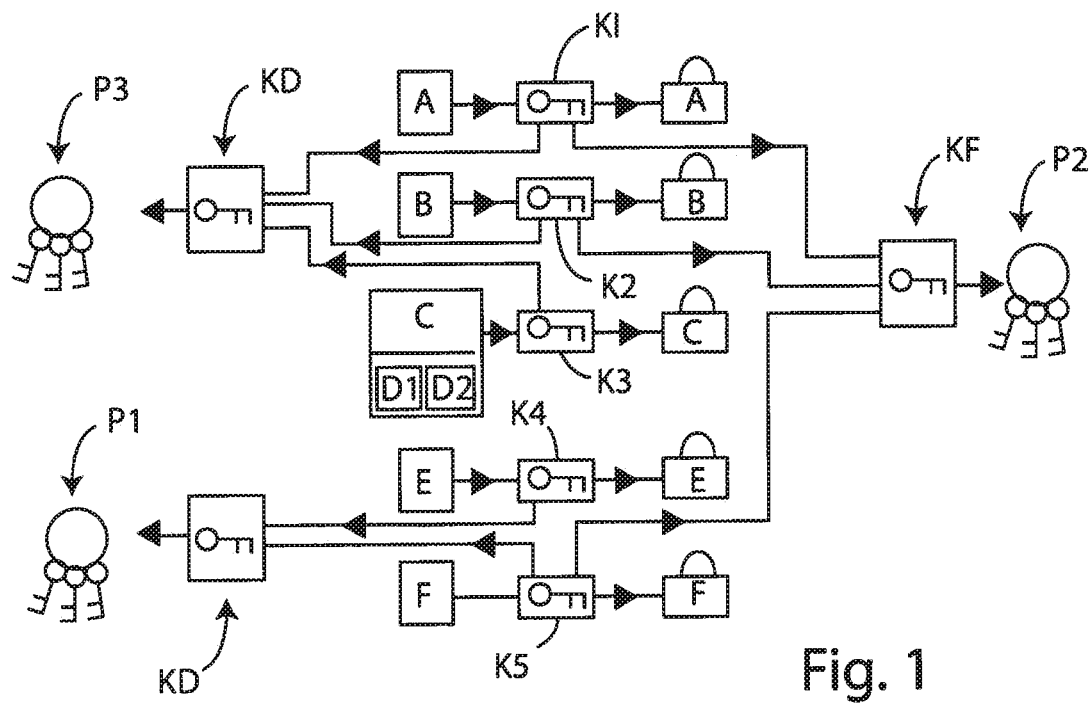
FIG. 1 illustrates a simplified and partial diagram of functioning of a device according to the invention.
Figure 2:
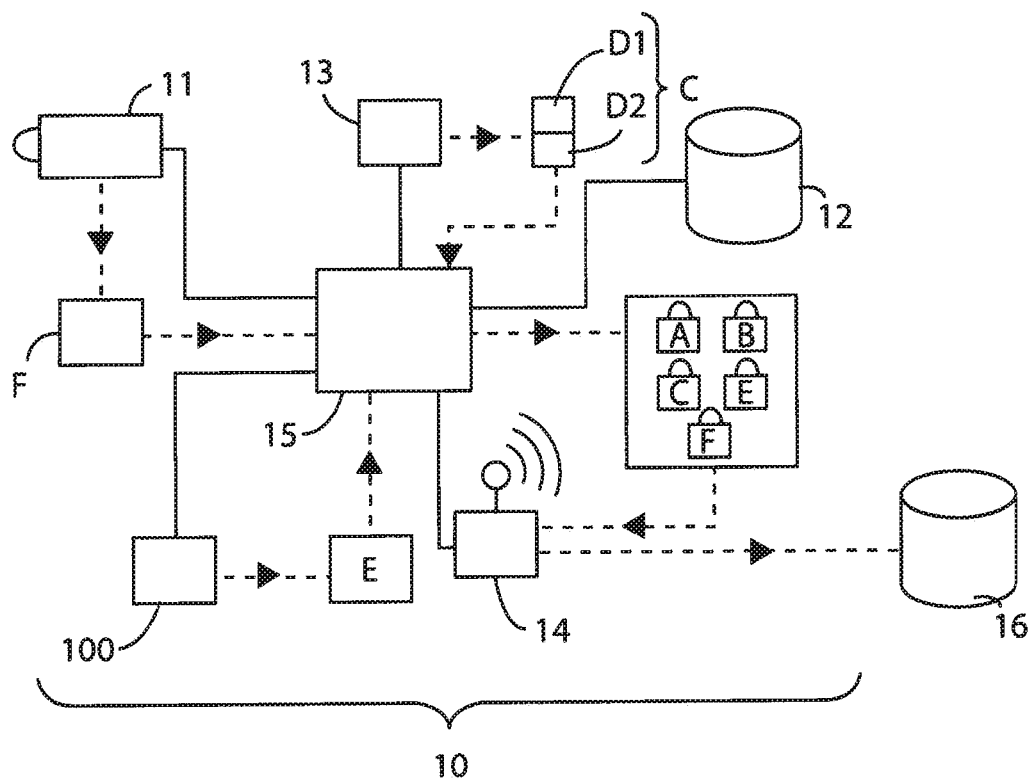
FIG. 2 illustrates a simplified diagram of the structure and functioning of a device according to the invention.

With particular reference to the figures mentioned, 10 indicates an apparatus for collecting medical data and particularly ophthalmoscopic data as a whole, particularly adapted to acquisition of images of the ocular fundus.

The present invention is illustrated below by way of non-limiting example with reference to the apparatus 10 for acquisition of ophthalmoscopic data and with reference to the method of acquisition of ophthalmoscopic data, but the scope of the invention itself is to be intended as general for any device and method for collecting medical data, such as, by way of non-limiting example, machines and methods for acquiring computerised axial tomography or machines and methods for analysis of blood or other bodily fluids.

In particular, the apparatus 10 is adapted to be given in use to an operator, who may be an ophthalmologist, who can perform a number of ophthalmoscopic examinations, i.e. a number of acquisitions of ophthalmoscopic data, predefined following a business agreement with the supplier of the apparatus 10.

In particular, said other party may be a supplier or a distributor of the apparatus 10.

Preferably, the number of ophthalmoscopic examinations performable will be a function of credit which the operator will have prepaid to the business partner or will be a function of credit quantified on the basis of business agreements.

Furthermore, the apparatus 10 will allow ophthalmoscopic examinations to be performed by any operator authorised by the business partner and who can use any apparatus 10 on the basis of the business agreements with said partner.

For example, a plurality of different doctors of a doctors' surgery may use the same apparatus 10, which will allow each different operator to perform examinations in the amount defined by the business agreements with the business partner.

Furthermore, a plurality of apparatuses 10, for example installed in different doctors' surgeries, may be used by the same operator, who may perform a total number of examinations, irrespective of the specific apparatus 10 used. Said total number of examinations, in totality, will be predefined according to the business agreements with the business partner.

The apparatus 10 is preferably provided with an interface 100 configured to allow identification of the operator and access to the medical and commercial data relating to said operator, which is stored in the apparatus 10.

The apparatus 10 is also advantageously connectable, for example via the global network, to a remote control device, in which a copy of the data present in the apparatus is stored or which stores the actual data in place of the apparatus 10.

Advantageously, the control device will be connectable to a plurality of apparatuses 10 by means of which the same operator, or a plurality of different operators, may connect to the control device to exchange with said device data on ophthalmoscopic examinations performed or data on usability of the apparatuses 10 as a function of the business agreements reached with the business partner.

Preferably, the apparatus 10 is configured to detect unauthorised use of it, for example use which infringes the agreements with the business partner, and is also configured to limit or block functioning of the apparatus 10 if said unauthorised use is detected, or is configured to prevent said unauthorised use.

Structurally, the apparatus 10 comprises an collecting device 11 adapted to acquire medical data and preferably images of an ocular fundus, and an electronic archive 12.

In accordance with the present invention, the apparatus 10 has a special feature in that it comprises:
- a counter device 13 to count the number of medical data acquisitions and preferably the images acquired;
- a transmission device 14;
- an electronic control device 15 connected to the collecting device 11, to the electronic archive 12, to the transmission device 14 and to the counter device 13, and configured to transmit the data acquired to the electronic archive 12 in digital format, organised in a predefined manner as specified better below.

The counter device 13 is advantageously configured to count the number of medical data acquisitions, and preferably images acquired, by means of the collecting device 11, and to provide the metering data to the control device 15, consisting in the calculation made by said counter device 13.

The transmission device 14 is adapted to exchange data in digital format with a remote device.

The control device 15 is configured to transmit, to the electronic archive 12, medical data organised into at least five groups of said ophthalmoscopic data.

Said data groups comprise:
- a first group comprising the personal data A relating to the operators of the apparatus 10;
- preferably a second group comprising the operating data B relating to the apparatus 10;
- a third group comprising the use data C, relating to authorisations for use of the apparatus 10 and comprising counting data D1 and D2 consisting in the effective calculation made by the counter device 13;
- a fourth group comprising the personal data E relating to the users of the apparatus 10;
- a fifth group comprising the biological data F acquired by the collecting device 11.

Preferably, the control device 15 is configured to associate the counting data D1, D2, with the first personal data A, which identifies each operator authorised to use the device 10 in such a manner that the number of medical data which each operator has acquired by means of the device 10 is associated with said operator.

Advantageously, the biological data F comprises photographic data consisting in images in digital format, acquired by the image collecting device 11.

In accordance with the embodiment described, reference will be made below to photographic data F, since the present description is valid, with the necessary changes, in general for biological data of any type, such as, by way of non-limiting example, graphic data relating to X-rays or to computerised axial tomography scans or to analytical tables of bodily fluids or tissues.

Preferably, the first personal data A comprises the operator's personal data, such as the name of the doctor to whom use of the apparatus 10 is given, and any data on the business agreements signed for use of said apparatus, such as preferably the data on the number of ophthalmoscopic examinations performable following payment of the relative amount of money to the partner.

The operating data B preferably comprises a serial number or identification number of the apparatus 10 and/or an identification number of the distributor of it and/or a historical register comprising a list of any anomalies of the apparatus 10.

The use data C preferably comprises the total examinations performable as a function of the agreements with the business partner and/or the total examinations performed with the apparatus 10.

The second personal data E advantageously comprises the personal data of each user examined by the apparatus 10.

The photographic data F advantageously comprises digital images of the ocular fundus of the users examined, provided with an identifier adapted to associate them with the personal data of said user comprised in the second personal data E.

The control device 15 is furthermore configured to:
- form packets of digital information, each comprising a plurality of data selected in a predefined manner from the data of said data groups;
- transmit said data packets to a remote device by means of the transmission device 14.

Advantageously, the control device 15 is configured to encrypt at least the second personal data E and the photographic data F of said data groups.

In a particularly preferred, but not exclusive, embodiment, the control device 15 is configured to encrypt only the second personal data E and the photographic data F, for faster access to said data packets.

In particular, said data packets preferably comprise a plurality of photographic data F, relating to a plurality of photographs of the ocular fundus taken of a user, associated with the second personal data E relating to said user.

The control device 15 is preferably configured to encrypt each group of said data groups with an encryption key K1, K2, K3, K4, K5, the encryption key K1, K2, K3, K4, K5 of each of said data groups being different to the encryption key K1, K2, K3, K4, K5 of each other group of said data groups.

In other words, each data group is advantageously encrypted with a different encryption key K1, K2, K3, K4, K5.

Preferably, a set of encryption keys of said data groups is provided, dedicated and exclusive for each operator authorised to access the apparatus 10, as a function of the agreements with the business partner. In other words, each set of encryption keys associated with each operator advantageously comprises different encryption keys to the encryption keys of the sets associated with each other authorised operator.

The control device 15 is advantageously configured to perform the following operations:
  generate a first virtual key-ring P1 comprising the encryption key K4 of the second personal data E and the encryption key K5 of the photographic data F, both encrypted by means of an encryption key for the operator KO;
  generate a second virtual key-ring P2 comprising the encryption key K1 of the first personal data A, the encryption key K5 of the photographic data F and the encryption key K3 of the use data C, and preferably also the encryption key K2 of the operating data B, encrypted by means of an encryption key for the supplier KF;
  generate a third virtual key-ring P3 comprising the encryption key K1 of the first personal data A and the encryption key K3 of the use data C, and preferably also the encryption key K2 of the operating data B, encrypted by means of an encryption key for the distributor KD.

Operatively, each operator will have an encryption key for the operator, customised, which allows access, by means of an apparatus 10, to the second personal data E and to the photographic data F present on the apparatus 10 itself or present on the remote device 16.

Preferably, encryption of data accessible by the operator will be configured in such a manner that said operator may share a selected set of data, for example of a particular patient, with another operator.

In this manner, a doctor can share with a colleague medical data of an individual patient, or a group of selected patients, without necessarily giving said colleague access to the data on all his patients.

The supplier of the apparatus 10 will be provided with the key for the supplier KF which will allow access to the first personal data A, to the operating data B and to the photographic data F stored in each apparatus 10 and/or in the remote device 16.

It should be noted that the supplier preferably will not have access to the second personal data E protecting the confidentiality of personal information of users of the apparatuses 10.

One embodiment of the apparatus 10, according to the invention, differs from the apparatus 10 described here solely in that the second personal data is preferably divided into two sub-groups, which is encrypted with different encryption keys.

In said embodiment, the first virtual key-ring comprises both said encryption keys of the two sub-groups, and the second virtual key-ring comprises solely one of said encryption keys of the two sub-groups, so that the supplier has access to only a predefined one of said two sub-groups, which comprises insufficient data to identify any user of the apparatus 10.

The operator is advantageously in possession of only the encryption key for the operator KO, the distributor is advantageously in possession of only the encryption key for the distributor KD and the supplier is advantageously in possession of only the encryption key for the supplier KF.

The apparatus 10 is preferably configured to modify one or more of said encryption keys.

Advantageously, the control device 15 is configured to store each photographic data F, acquired by the collecting device 11, selectively in a first sub-group or in a second sub-group of the photographic data F.

The first sub-group comprises photographic data F for which the operator has activated a save command, said second sub-group comprising photographic data F for which the operator has activated a reject command.

The counter device 13 is advantageously configured to count further the number of photographic data F stored in said second sub-group; said counting data D1 and D2 comprising:
  first counting data D1 consisting in the number of images acquired by the collecting device 11;
  second counting data D2 consisting in the number of photographic data F stored in said first sub-group or in the number of photographic data F stored in said second sub-group.

Preferably the counting data D1 and D2 is associated with each operator identified by the first personal data A in a manner that the supplier and/or the distributor are able to check the number of acquisitions made by each operator, irrespective of whether the result of said acquisitions has been saved or rejected.

The control device 15 also comprises counting means, not shown, for counting the ophthalmoscopic data acquisitions performable, said counting means being configured to calculate the difference between
  a predefined number of acquisitions performable, and
  a number of photographic data F stored in the electronic archive 12 subsequently to a predefined time reference.

The control device 15 is preferably configured to prevent or limit functioning of the apparatus 10 if said difference is zero.

Said predefined number of acquisitions performable is advantageously set as a function of business agreements between the operator and the business partner.

The predefined time reference will preferably be the date on which the operator has paid an amount of cash defining said number of performable acquisitions.

Advantageously, the device 10 is configured to implement the encryption system of the ophthalmoscopic data acquired, known as client side encryption.

A further object of the present invention is a medical data acquisition method, and preferably ophthalmoscopic data, which has a special feature in that it comprises:
  acquiring medical data and preferably ophthalmoscopic data, by means of the apparatus 10;
  storing a copy of said medical data, preferably ophthalmoscopic data, acquired in the remote device 16, separate from the apparatus 10;
  assessing the methods of use of the apparatus 10 by means of a predefined algorithm comparing the medical data, preferably ophthalmoscopic data, comprised in the last copy stored and the medical data, preferably ophthalmoscopic data, comprised in the penultimate copy stored;
  limiting or blocking functioning of the apparatus 10 if the methods of use assessed correspond with predefined prohibited methods of use.

Preferably, the data acquisition phase, preferably ophthalmoscopic data, comprises:
recording, for each biological data and preferably photographic data F, a save command or a reject command, settable by the operator;
storing in apparatus 10 each photographic data F selectively.

In particular, said step of archiving each photographic data F selectively envisages storing
in a first sub-group of photographic data F the photographic data for which the save command is recorded;
in a second sub-group of photographic data F the photographic data for which the reject command is recorded.

Advantageously, the step of acquiring ophthalmoscopic data comprises organising counting data D1 and D2 comprising:
first counting data D1 consisting in the number of images acquired by the collecting device 11;
second counting data D2 consisting in the number of photographic data F stored in said first sub-group or in the number of photographic data F stored in said second sub-group.

The step of assessing the methods of use of the apparatus 10 advantageously envisages:
calculation of a first difference between the first calculation data comprised in the last copy of the ophthalmoscopic data stored and the first calculation data comprised in the penultimate copy of the ophthalmoscopic data stored;
calculation of a second difference between the second calculation data comprised in the last copy of the ophthalmoscopic data stored and the second calculation data D2 comprised in the penultimate copy of the ophthalmoscopic data stored;
calculation of a third difference between the value of said first difference and the value of said second difference.

The step of limiting or blocking functioning of said apparatus 10, advantageously comprises checking whether the value of said third difference is equal to the values of predefined alarms.

In particular, the step of limiting or blocking functioning of the apparatus 10 advantageously envisages limiting or blocking functioning of the apparatus 10 if the value of said third difference is equal to the values of predefined alarms.

The control device 10 is advantageously configured to limit or block functioning of the apparatus 10 if the value of the first calculation data exceeds beyond a predefined value the number of data stored in the first sub-group.

In other words, the control device is preferably configured to limit or block at least several functions of the apparatus 10 if the operator acquires many more images than they save, since said use of the apparatus 10 could indicate a fraud or malfunctioning of said apparatus.

The present method of acquisition of ophthalmoscopic data according to the invention preferably comprises:
setting a number of acquisitions performable by means of the apparatus 10;
calculating a number of ophthalmoscopic data acquisitions performed, by means of the apparatus 10, subsequently to the step of setting a number of acquisitions performable;
limiting or blocking use of the apparatus 10 if the number of acquisitions performed is equal to or higher than the number of performable acquisitions.

The number of acquisitions performed is advantageously equal to the number of data stored in said fist sub-group subsequently to the step of setting a number of performable acquisitions.

In other words, the acquisitions performable advantageously consists in a number of examinations for which the operator has prepaid an agreed amount and, therefore, the number of acquisitions performed is preferably the number of examinations completed subsequently to the last credit top-up or the last payment of a prepayment amount of a corresponding number of examinations.

The invention as it is conceived is susceptible to numerous modifications and variants, all falling within the scope of the appended claims.

Furthermore all the details can be replaced by other technically equivalent elements.

In practice, the materials used, as well as the contingent shapes and dimensions, can be varied according to the contingent requirements and the state of the art.

Where the construction characteristics and techniques mentioned in the subsequent claims are followed by signs or reference numbers, such signs or reference numbers have been used for the sole aim of increasing the intelligibility of the claims themselves and, therefore, they do not in any way constitute a limitation to the interpretation of each identification element, purely by way of example, by such signs or reference numbers.

The invention claimed is:

1. An apparatus (10) for collecting medical data comprising:
an ocular fundus image collecting device (11);
an electronic archive (12);
a counter device (13) configured to count the number of ocular fundus image acquisitions performed by said ocular fundus image collecting device (11);
a transmission device (14) adapted to exchange data in digital format with a remote device;
an electronic control device (15) connected to said ocular fundus image collecting device (11), to said electronic archive (12), to said counter device (13) to receive counting data (D1, D2) the calculation made by said counter device (13), to said transmission device (14) and configured to transmit, to said electronic archive (12), medical data in digital format in a mode organized into at least five groups of said medical data, which comprise:
first personal data (A) relating to the operators of said apparatus (10);
use data (C), relating to authorizations for use of said apparatus (10) and comprising said counting data (D1, D2) associated with said operators;
second personal data (E) relating to the users of said apparatus (10); and
biological data (F) in digital format; said control device (15) also being configured to:
form packets of digital information, each comprising a plurality of data selected in a predefined manner from the data of said data groups, and
transmit said data packets to a remote device by-means of the transmission device (14) wherein the apparatus (10) allows a predefined number of ophthalmoscopic examinations to be performed by an operator as a function of credit quantified on the basis of business agreements, the use data (C) comprising the total examinations performable as a function of the business agreements and/or the total examinations performed with the apparatus (10), said control device (15) is configured to calculate the difference between a predefined number of acquisitions performable, and a number of biological data (F) stored in said electronic archive (12) subsequently to a predefined time reference; said control device (15) being configured to prevent functioning of said apparatus (10) if said difference is zero or negative.

2. The medical data collecting apparatus (10) according to claim 1, wherein said data groups further comprise operating data (B), relating to said apparatus (10).

3. The medical data collecting apparatus (10) according to claim 1, wherein said control device (15) is further configured to encrypt at least said second personal data (E) and said biological data (F) of said data groups.

4. The medical data collecting apparatus (10) according to claim 2, wherein said control device (15) is configured to encrypt each group of said data groups with an encryption key (K1, K2, K3, K4, K5); the encryption key (K1, K2, K3, K4, K5) of each of said data groups being different to the encryption key (K1, K2, K3, K4, K5) of each other group of said data groups.

5. The medical data collecting apparatus (10) according to claim 3, wherein said control device (15) is configured to
generate a first virtual key-ring (PI) comprising the encryption key (K4) of the second personal data (E) and the encryption key (K5) of said biological data (F), both encrypted by means of an encryption key for the operator (KO);
generate a second virtual key-ring (P2) comprising the encryption key (1) of said first personal data (A), the encryption key (K6) of said biological data (F) and the encryption key (K3) of the use data C, encrypted by means of an encryption key for the supplier (F);
generate a third virtual key-ring (P3) comprising the encryption key (K1) of said first personal data (A) and the encryption key (K3) of said use data (C), encrypted by means of an encryption key for the distributor (KD).

6. The medical data collecting apparatus (10) according to claim 2, wherein said second virtual key-ring (P2) comprises the encryption key (K2) of said operating data (B), and that said third virtual key-ring comprises the encryption key (K2) of said operating data (B).

7. The medical data collecting apparatus (10) according to claim 1, wherein said control device (15) is configured to store each of said biological data (F), acquired by said ocular fundus image collecting device (11), selectively in a first subgroup or in a second sub-group of said biological data (F), said first sub-group comprising biological data(F) for which the operator has activated a save command; said second sub-group comprising biological data(F) for which the operator has activated a reject command; said counter device (13) being configured to count further the number of biological data (F) stored in said second sub-group; said counting data (D1, D2) comprising:
first counting data (D1) consisting in the number of biological data (F) acquired by the ocular fundus image collecting device (11);
second counting data (D2) consisting in the number of biological data (F) stored in said first subgroup or in the number of biological data (F) stored in said second sub-group.

8. The medical data collecting apparatus (10) according to claim 1, wherein said ocular fundus image collecting device (11) is configured for acquisition of images of the ocular fundus, said biological data comprising said images of the ocular fundus; said counter device (13) being configured to count the number of said images of the ocular fundus acquired by means of said ocular fundus image collecting device (11); said biological data (F) comprising photographic data consisting in images of the ocular fundus in electronic format.

9. A medical data acquisition method, wherein it comprises:
providing a medical data collecting apparatus (10) according to claim 1;
using the medical data collecting apparatus (10) to acquire medical data;
archiving a copy of said medical data in a remote device (16), which is separate from said apparatus (10);
assessing the methods of use of the apparatus (10) by means of a predefined algorithm comparing the medical data comprised in a last stored copy of said medical data and the medical data comprised in a penultimate stored copy of said medical data;
limiting or blocking functioning of said apparatus (10) if said methods of use assessed correspond with predefined prohibited methods of use;
allowing a predefined number of opthalmoscopic examinations to be performed by an operator as a function of credit for which the operator has prepaid and/or as a function of credit quantified on the basis of business agreements.

10. The medical data acquisition method according to claim 9, wherein said medical data acquisition step comprises:
recording, for each biological data (F) of said medical data, a save command or a reject command, settable by the operator;
storing in said apparatus (10) each biological data (F) selectively in a first sub-group or in a second sub-group of said biological data (F), storing in said first sub-group the biological data (F) for which said save command is recorded and in said second sub-group the biological data (F) for which said reject command is recorded.

11. The medical data acquisition method according to claim 10, wherein said medical data acquisition step comprises organizing counting data, the counting data comprising:
first counting data (D1) of the number of biological data (F) acquired by the ocular fundus image collecting device (11);
second counting data (D2) of the number of biological data (F) stored in said first sub-group or in the number of biological data (F) stored in said second sub-group.

12. The medical data acquisition method according to claim 11, wherein said step of assessing the methods of use of said apparatus (10) comprises:
calculation of a first difference between the first counting data (D1) of the last copy of the medical data stored and the first counting data (D1) of the penultimate copy of the medical data stored;
calculation of a second difference between the second counting data (D2) of the last copy of the medical data stored and the second counting data (D2) of the penultimate copy of the medical data stored; and
calculation of a third difference between the value of said second difference and the value of said first difference.

13. The medical data acquisition method according to claim 12, wherein said step of limiting or blocking functioning of said apparatus (10) comprises checking whether the value of said third difference is equal to the predefined alarm values.

14. The medical data acquisition method according to claim 9, further comprising:

setting a number of acquisitions performable by means of the apparatus (10);

calculating a number of medical data acquisitions performed, by means of the apparatus (10), subsequently to the step of setting a number of acquisitions performable; and limiting or blocking the use of said apparatus (10) if said number of acquisitions performed is equal to or higher than the number of performable acquisitions.

15. The medical data acquisition method according to claim 10, wherein said number of acquisitions performed is equal to the number of data stored in said first sub-group subsequently to said step of setting a number of acquisitions performable.

16. The medical data acquisition method according to claim 10, wherein said medical data comprises ophthalmoscopic data said biological data (F) comprising photographic data of images of the ocular fundus in electronic format.

* * * * *